US012616836B2

(12) United States Patent
Yeon

(10) Patent No.: US 12,616,836 B2
(45) Date of Patent: May 5, 2026

(54) METHOD FOR TREATING BACTERIAL AND VIRAL DISEASES USING ELECTRICAL STIMULATION

(71) Applicant: SEOUL NATIONAL UNIVERSITY R&DB FOUNDATION, Seoul (KR)

(72) Inventor: Seong Chan Yeon, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 375 days.

(21) Appl. No.: 17/927,956

(22) PCT Filed: Jan. 21, 2021

(86) PCT No.: PCT/KR2021/000824
§ 371 (c)(1),
(2) Date: Nov. 28, 2022

(87) PCT Pub. No.: WO2021/241839
PCT Pub. Date: Dec. 2, 2021

(65) Prior Publication Data
US 2023/0201587 A1      Jun. 29, 2023

(30) Foreign Application Priority Data

| May 27, 2020 | (KR) | ......................... | 10-2020-0063423 |
| Jan. 15, 2021 | (KR) | ......................... | 10-2021-0005932 |

(51) Int. Cl.
*A61N 1/36* (2006.01)
(52) U.S. Cl.
CPC ..... *A61N 1/36034* (2017.08); *A61N 1/36031* (2017.08)

(58) Field of Classification Search
CPC ............ A61N 1/36034; A61N 1/36031; A61N 1/0484; A61N 1/36014; A61N 2/00;
(Continued)

(56) References Cited

U.S. PATENT DOCUMENTS

| 5,690,692 A | * | 11/1997 | Fleming | ................. | A61N 1/326 |
| | | | | | 607/66 |
| 6,424,864 B1 | * | 7/2002 | Matsuura | ........... | A61H 23/0245 |
| | | | | | 607/66 |

(Continued)

FOREIGN PATENT DOCUMENTS

| EP | 1 040 847 A1 | 10/2000 | |
| EP | 2252242 B1 | * 4/2016 | ............... A61F 5/01 |

(Continued)

OTHER PUBLICATIONS

List of diseases caused by bacteria. MicroscopeMaster. (Oct. 2016). https://www.microscopemaster.com/list-of-diseases-caused-by-bacteria.html, hereinafter Microscope Master (Year: 2016).*

(Continued)

*Primary Examiner* — Michael W Kahelin
*Assistant Examiner* — Attiya Sayyada Hussaini
(74) *Attorney, Agent, or Firm* — The PL Law Group, PLLC

(57) ABSTRACT

A method for treating at least one of a bacterial disease and a viral disease according to an embodiment includes sequentially generating electrical stimulation at different frequencies, and sequentially applying the generated electrical stimulation at different frequencies to user's body through an electrode unit in contact with the body of a user who has the bacterial or viral disease.

12 Claims, 8 Drawing Sheets

(58) Field of Classification Search

CPC .......... A61N 2/02; A61N 1/0408; A61N 1/08; A61N 1/20; Y02A 50/30; A61B 5/0002; A61B 5/01; A61B 5/024; A61B 5/14542; A61B 5/443; A61B 5/4836; A61B 2503/40

See application file for complete search history.

(56) References Cited

U.S. PATENT DOCUMENTS

| | | | | |
|---|---|---|---|---|
| 7,272,440 | B2 * | 9/2007 | Silverstone | ........ A61N 1/36034 |
| | | | | 607/2 |
| 2004/0181264 | A1 | 9/2004 | Silverstone | |
| 2007/0123807 | A1 * | 5/2007 | Applebaum | ......... A61H 39/002 |
| | | | | 601/19 |
| 2017/0319844 | A1 * | 11/2017 | Woo | ...................... A61N 1/0456 |
| 2022/0331582 | A1 * | 10/2022 | Kim | ................... A61N 1/36014 |

FOREIGN PATENT DOCUMENTS

| | | | |
|---|---|---|---|
| KR | 200370758 | Y1 * | 12/2004 |
| KR | 20-0414456 | Y1 | 4/2006 |
| KR | 10-1061009 | B1 | 9/2011 |
| KR | 20-2012-0007148 | U | 10/2012 |
| KR | 10-2019-0130089 | A | 11/2019 |
| WO | WO 2015/179571 | A1 | 11/2015 |

OTHER PUBLICATIONS

KR200370758Y1_Translation (Year: 2003).*

Preventing *Escherichia coli* (*E. coli*) Infections.ă Appledore Medical Group, 2018, appledoremedicalgroup.com/blog/entry/preventing-escherichia-coli-e-coli-infections. Accessed Sep. 23, 2025 (Year: 2018).*

Bedard, Kristin M., and Bert L. Semler. "Regulation of picornavirus gene expression." Microbes and Infection 6.7 (2004): 702-713. (Year: 2004).*

Electrotherapy Device Frequency List (ETDFL) (Year: 2017).*

User Manual for RIFE ETD (Year: 2017).*

International Search Report for PCT/KR2021/000824 mailed on Apr. 27, 2021.

Office action issued on Mar. 8, 2023 from Korean Patent Office in a counterpart Korean Patent Application No. 10-2021-0005932.

* cited by examiner

METHOD FOR TREATING BACTERIAL AND VIRAL DISEASES USING ELECTRICAL STIMULATION

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2021/000824 filed on Jan. 21, 2021, which claims priority to the benefit of Korean Patent Application Nos. 10-2020-0063423 filed on May 27, 2020 and 10-2021-0005932 filed on Jan. 15, 2021 in the Korean Intellectual Property Office, the entire contents of which are incorporated herein by reference.

BACKGROUND

1. Technical Field

The present invention relates to a method for treating bacterial and viral diseases using electrical stimulation.

2. Background Art

A virus refers to an infectious agent including a genetic material composed of DNA or RNA and a protein. Sizes of viruses vary depending on types thereof, but usually range from 10 to 1000 nm. Since the viruses cannot metabolize themselves, after infiltrating their DNA or RNA into host cells such as bacteria, animals or plants, the DNAs or RNAs are replicated using organelles of the host cell to produce viruses like themselves, and thereby usually resulting in destruction of the host cell.

In spite of the defensive power (immune response) of the human body, bacteria and viruses have remarkably fast mutation rates, such that new bacteria and viruses are continuously produced. Due to the fast mutation rates, it is difficult to develop therapeutic agents and vaccines for treating diseases caused by the bacteria and viruses. Thereby, there is no choice but to perform conservative treatments until a vaccine is developed, resulting in high number of casualties. Accordingly, there is an increasing need to develop a treatment method capable of primarily killing or reducing bacteria and viruses that have infiltrated the body using a specific combination such as current, voltage, frequency, waveform, energization time and the like.

SUMMARY

It is an object of the present invention to provide a method for treating bacterial and viral diseases using electrical stimulation.

To achieve the above objects, according to an aspect of the present invention, there is provided a method for treating bacterial and viral diseases, the method including: sequentially generating electrical stimulation at different frequencies; and sequentially applying the generated electrical stimulation at different frequencies to user's body through an electrode unit in contact with the body of a user who has the bacterial or viral disease.

The bacterial or viral disease may include rhinitis.

The electrical stimulation may include a voltage or current, wherein the voltage may be greater than 0 and 300 V or less, the current may be greater than 0 and 12 mA or less, a frequency of the electrical stimulation may be 1 Hz or more and 100 GHz or less, a duration of each frequency may be 1 minute or more and 20 minutes or less, and a waveform of the electrical stimulation may be any one of direct current, alternating current, and pulsation or a combination of two or more thereof.

The generating step may include sequentially generating the electrical stimulation at different frequencies with reference to a pre-stored frequency list. The method may further include measuring a temperature or humidity of user's skin in contact with the electrode unit. The method may further include stopping generation of the electrical stimulation when the measured temperature or humidity is a set level or more.

The bacterial disease may include diseases resulting from pneumococcus, pyogenic bacteria, gonorrhea, brucellosis, *E. coli*, tubercular *bacillus*, typhoid *bacillus*, cholera bacteria, *Treponema pallidum, Staphylococcus aureus, Staphylococcus* and *Salmonella*.

The viral disease may include diseases resulting from human papilloma virus, Ebola virus, coronavirus, SARS virus, measles virus, human immunodeficiency virus (HIV), Japanese encephalitis virus, hepatitis A, B and C viruses, herpes virus, rabies virus, influenza virus, Rhino virus, respiratory syncytial virus (RSV), flu virus, Zika virus, West Nile virus, variola virus and polio virus.

By sequentially applying electrical stimulation at different frequencies to the body of a user who has the bacterial or viral disease, it is possible to kill or reduce bacteria and viruses that have infiltrated the body of the user.

BRIEF DESCRIPTION OF THE DRAWINGS

FIG. 4 is a view illustrating a state in which a band unit shown in FIG. 3 is worn on the user's wrist;

DETAILED DESCRIPTION

Figure 1:
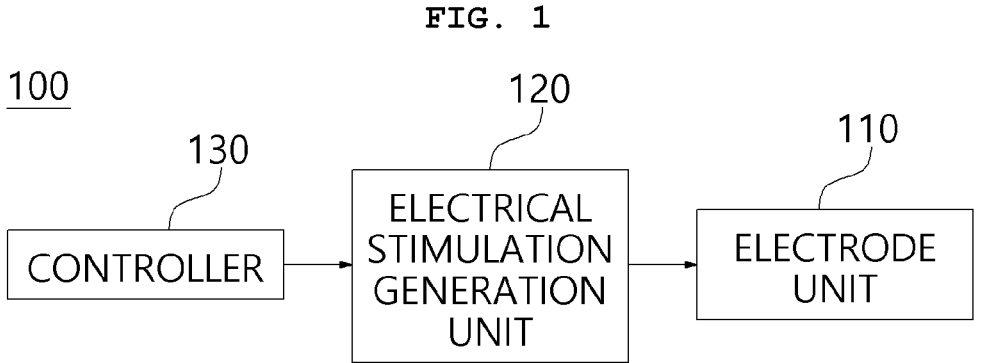
FIG. 1 is a block diagram illustrating a device for treating bacterial and viral diseases using electrical stimulation according to an exemplary embodiment.

Hereinafter, embodiments will be described in detail with reference to the accompanying drawings. In denoting reference numerals to components of respective drawings, it should be noted that the same components will be denoted by the same reference numerals although they are illustrated in different drawings. Further, in description of preferred embodiments of the present invention, the publicly known functions and configurations related to the present invention, which are verified to be able to make the purport of the present invention unnecessarily obscure will not be described in detail.

Meanwhile, in respective steps, each of the steps may occur differently from the specified order unless a specific order is clearly described in the context. That is, each of the steps may be performed in the same order as the specified order, may be performed substantially simultaneously, or may be performed in the reverse order.

Further, wordings to be described below are defined in consideration of the functions in the present invention, and may differ depending on the intentions of a user or an operator or custom. Accordingly, such wordings should be defined on the basis of the contents of the overall specification.

It will be understood that, although the terms first, second, etc. may be used herein to describe various components, but these components should not be limited by these terms. These terms are used only to distinguish one component from other components. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

In addition, a division of the configuration units in the present disclosure is intended for ease of description and divided only by the main function set for each configuration unit. That is, two or more of the configuration units to be described below may be combined into a single configuration unit or formed by two or more of divisions by function into more than a single configuration unit. Further, each of the configuration units to be described below may additionally perform a part or all of the functions among functions set for other configuration units other than being responsible for the main function, and a part of the functions among the main functions set for each of the configuration units may be exclusively taken and certainly performed by other configuration units. Each of the configuration units to be described below may be implemented as hardware or software, or may be implemented as a combination of hardware and software.

FIG. 1 is a block diagram illustrating a device for treating bacterial and viral diseases using electrical stimulation according to an exemplary embodiment.

Referring to FIG. 1, a device 100 for treating bacterial and viral diseases using electrical stimulation (hereinafter, referred to as a disease treatment device) may include an electrode unit 110, an electrical stimulation generation unit 120 and a controller 130.

The electrode unit 110 may come into contact with a body of a user who has the bacterial or viral disease to apply electrical stimulation to the user's body. Herein, the user's body may include a wrist, an ankle, a forearm, a calf, a thigh, a finger, a waist, a neck, and the like, but it is not limited thereto. In addition, the electrical stimulation includes a voltage or current, and it is possible to transmit a microcurrent of less than 1000 µA to the user's body through the electrical stimulation.

The bacterial or viral disease may include rhinitis. In addition, the bacterial disease may include, for example, diseases resulting from pneumococcus, pyogenic bacteria, gonorrhea, brucellosis, *E. coli*, tubercular *bacillus*, typhoid *bacillus*, cholera bacteria, *Treponema pallidum, Staphylococcus aureus, Staphylococcus* and *Salmonella*, etc., and the viral disease may include, for example, diseases resulting from human papilloma virus, Ebola virus, coronavirus, SARS virus, measles virus, human immunodeficiency virus (HIV), Japanese encephalitis virus, hepatitis A, B and C viruses, herpes virus, rabies virus, influenza virus, Rhino virus, respiratory syncytial virus (RSV), flu virus, Zika virus, West Nile virus, variola virus and polio virus, etc. Herein, the human papilloma virus (HPV) may include, for example, types HPV 6, HPV 11, HPV 16, HPV 18, HPV 31, HPV 33, HPV 45, HPV 52 and HPV 58, etc., and the coronavirus may include, for example, SARS-CoV, MERS-CoV, SARS-CoV-2 and SARS-like-CoV, etc.

According to an embodiment, the electrode unit 110 may include a plurality of electrodes which come into contact with different body regions of the user, and each electrode may be made of a conductive material through which electricity can flow, for example, conductive metal, conductive rubber, conductive plastic and the like.

The electrical stimulation generation unit 120 may sequentially generate electrical stimulation at different frequencies under the control of the controller 130 and transmit it (i.e., the generated electrical stimulation) to the electrode unit 110. At this time, in the electrical stimulation, the voltage may be greater than 0 and 300 V or less, the current may be greater than 0 and 12 mA or less, the frequency may be 1 Hz or more and 100 GHz or less, and the duration, i.e., energizing time of each frequency may be 1 minute or more and 20 minutes or less. The waveform of the electrical stimulation may be any one of direct current, alternating current, and pulsation (monophasic or biphasic pulse) or a combination of two or more thereof.

According to an embodiment, the electrical stimulation generation unit 120 may use a pre-stored frequency list. In this case, the electrical stimulation generation unit 120 may sequentially and repeatedly generate electrical stimulation at each frequency in the frequency list.

For example, it is assumed that three frequencies (a first frequency to a third frequency) are registered in the frequency list and the duration of electrical stimulation at each frequency is set to be 1 minute. In this case, the electrical stimulation generation unit 120 may generate electrical stimulation at the first frequency for 1 minute and transmit it to the electrode unit 110, generate electrical stimulation at the second frequency for 1 minute and transmit it to the electrode unit 110, and generate electrical stimulation at the third frequency for 1 minute and transmit it to the electrode unit 110, and then generate electrical stimulation at the first frequency again for 1 minute and transmit it to the electrode unit 110. In this way, the electrical stimulation generation unit 120 may sequentially and repeatedly generate the electrical stimulation at each frequency in the frequency list and apply it to the user through the electrode unit 110.

Meanwhile, the electrical stimulation generation unit 120 may generate electrical stimulation using a power source or a battery equipped inside or outside the disease treatment device 100.

The controller 130 may control an overall operation of the disease treatment device 100. Further, the controller 130 may perform various calculations executed by the disease treatment device 100 and process data. In addition, the controller 130 may be configured to drive an operating system (OS), an application, and the like for driving the disease treatment device 100. For example, when a command or a predetermined event is generated from the user, the controller 130 may control the electrical stimulation generation unit 120 to sequentially generate electrical stimulation at different frequencies and transmit it to the electrode unit 110.

Figure 2:
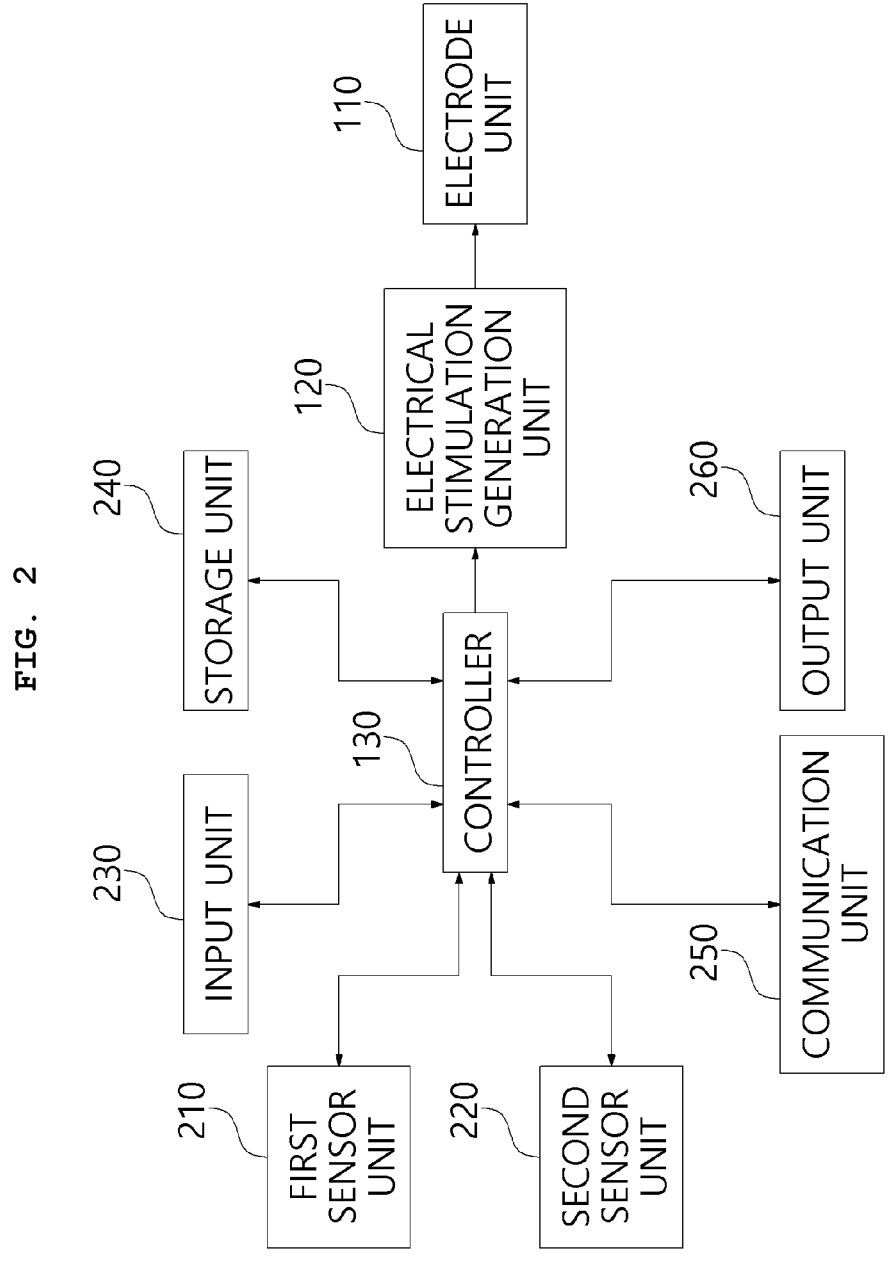
FIG. 2 is a block diagram illustrating a device for treating bacterial and viral diseases using electrical stimulation according to another exemplary embodiment.

FIG. 2 is a block diagram illustrating a device for treating bacterial and viral diseases using electrical stimulation according to another exemplary embodiment.

Referring to FIG. 2, a disease treatment device 200 may include an electrode unit 110, an electrical stimulation generation unit 120, a controller 130, a first sensor unit 210, a second sensor unit 220, an input unit 230, a storage unit 240, a communication unit 250, and an output unit 260. Herein, the electrode unit 110, the electrical stimulation generation unit 120 and the controller 130 are the same as those described above with reference to FIG. 1, and therefore will not be described in detail.

The first sensor unit 210 may measure environmental information of the user's skin. Herein, the environmental information may include temperature and humidity. To this end, the first sensor unit 210 may include a temperature sensor and a humidity sensor, etc.

When the electrode unit 110 comes into contact with a body surface, that is, the skin of the user for a long period of time, the skin temperature is increased or sweat is discharged from the skin, such that a desired microcurrent cannot be properly transmitted to the user's body. Accordingly, when at least one of the temperature and humidity measured by the first sensor unit 210 is a set level or more due to the heat and sweat generated from the user's body, the controller 130 may stop the operation of the electrical stimulation generation unit 120, or notify the user that the value measured by the first sensor unit 210 is the set level or more through an output unit 260 to be described below.

The second sensor unit 220 may come into contact with the user's body to measure biosignals. Herein, the biosignal may include a body temperature, a heart rate, a pulse, a blood pressure, an electrocardiogram or the like. To this end, the second sensor unit 220 may include a body temperature sensor, a heart rate sensor, a pulse sensor, a blood pressure sensor and an electrocardiogram sensor, etc. The user's biosignal measured by the second sensor unit 220 is transmitted to an external device through the communication unit 250 to be described below, then may be used for monitoring physical conditions of the user.

The input unit 230 may receive various operational signals and information input from the user. According to an embodiment, the input unit 230 may include a key pad, a dome switch, a touch pad, a jog wheel, a jog switch, a hardware/software (H/W) button or the like. In particular, when the touch pad forms a layer structure together with a display, it may be referred to as a touch screen.

The storage unit 240 may store a program or commands for an operation of the disease treatment device 200, and may store data input/output to/from the disease treatment device 200, processed data and the like. For example, the storage unit 240 may store information necessary for generating electrical stimulation used for treatment of bacterial or viral diseases, such as a voltage magnitude, a current magnitude, a frequency list, a duration of each frequency, an electrical stimulation waveform (e.g., direct current, alternating current, pulsation (monophasic or biphasic pulse, etc.) and the like. In addition, the storage unit 240 may store the environmental information measured by the first sensor unit 210 and the biosignal measured by the second sensor unit 220.

The storage unit 240 may include at least one type of storage medium such as a flash memory type, a hard disk type, a multimedia card micro type, or a card type memory (e.g., SD or XD memory, etc.), Random Access Memory (RAM), Static Random Access Memory (SRAM), Read Only Memory (ROM), Electrically Erasable Programmable Read Only Memory (EEPROM), Programmable Read Only Memory (PROM), magnetic memory, magnetic disk, optical disk and the like. Further, the disease treatment device 200 may operate an external storage medium such as a web storage medium which performs the storage function of the storage unit 240 on the Internet.

The communication unit 250 may perform communication with the external device. For example, the communication unit 250 may transmit data, etc., which are input, stored, or processed in the disease treatment device 200 to the external device, or may receive various data to be used for treatment of bacterial or viral diseases from the external device.

The communication unit 250 may communicate with the external device using the wired and/or wireless communication technique. At this time, the wireless communication technique may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, ultra-wideband (UWB) communication, Ant+communication, WIFI communication, Radio Frequency Identification (RFID) communication, 3G communication, 4G communication, 5G communication, or the like, but it is not limited thereto.

The output unit 260 may output data, etc., which are input, stored, or processed in the disease treatment device 200. According to an embodiment, the output unit 260 may output electrical stimulation information (e.g., voltage magnitude, current magnitude, frequency, duration of each frequency, waveform) applied to the user, environmental information measured by the first sensor unit 210, and the biosignal measured by the second sensor unit 220 using at least one of an auditory method, a visual method, and a tactile method. To this end, the output unit 260 may include a display, a speaker, a vibrator and the like.

Figure 3:
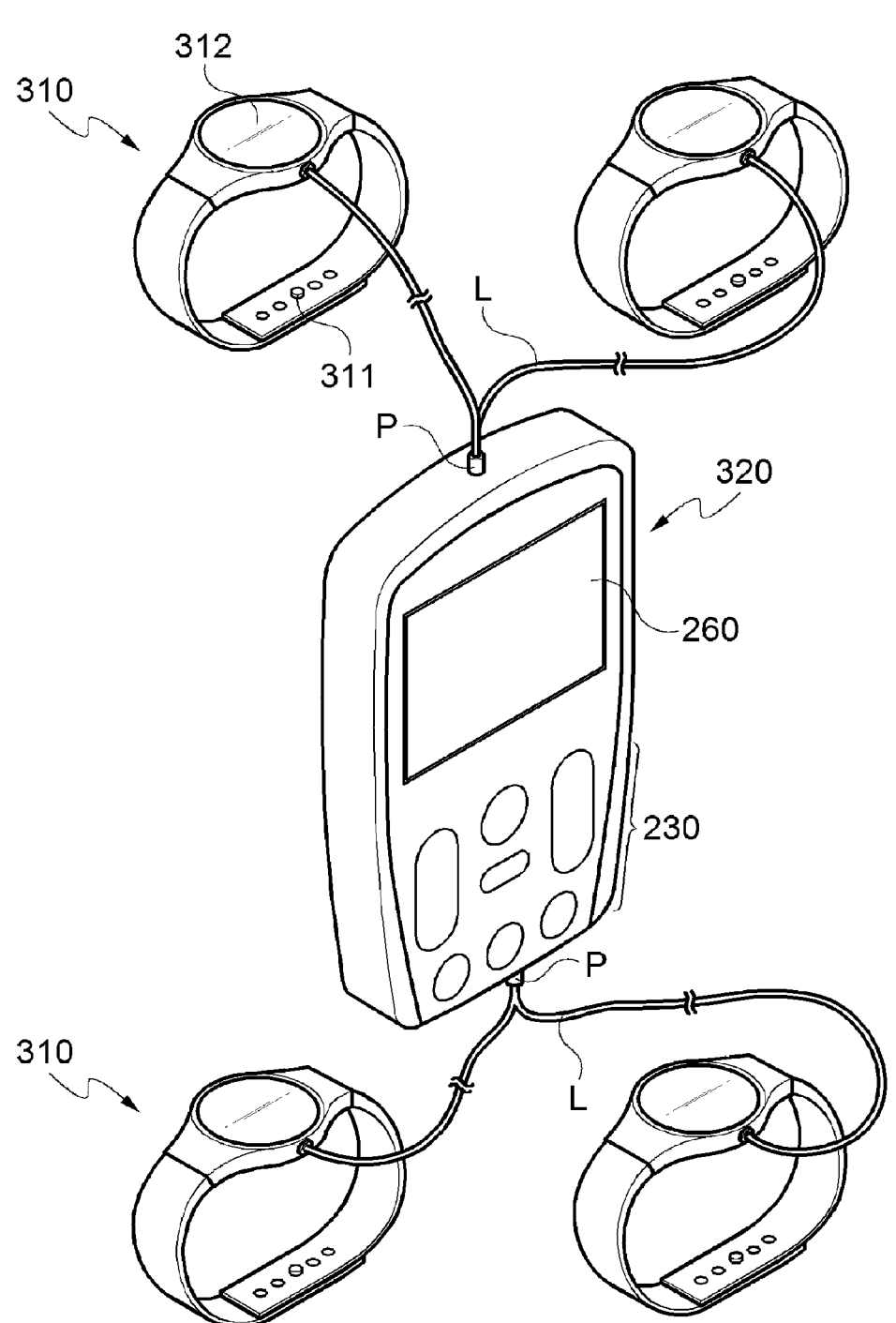
FIG. 3 is a perspective view illustrating an embodiment of the device for treating bacterial and viral diseases using electrical stimulation according to an exemplary embodiment.
Figure 4:
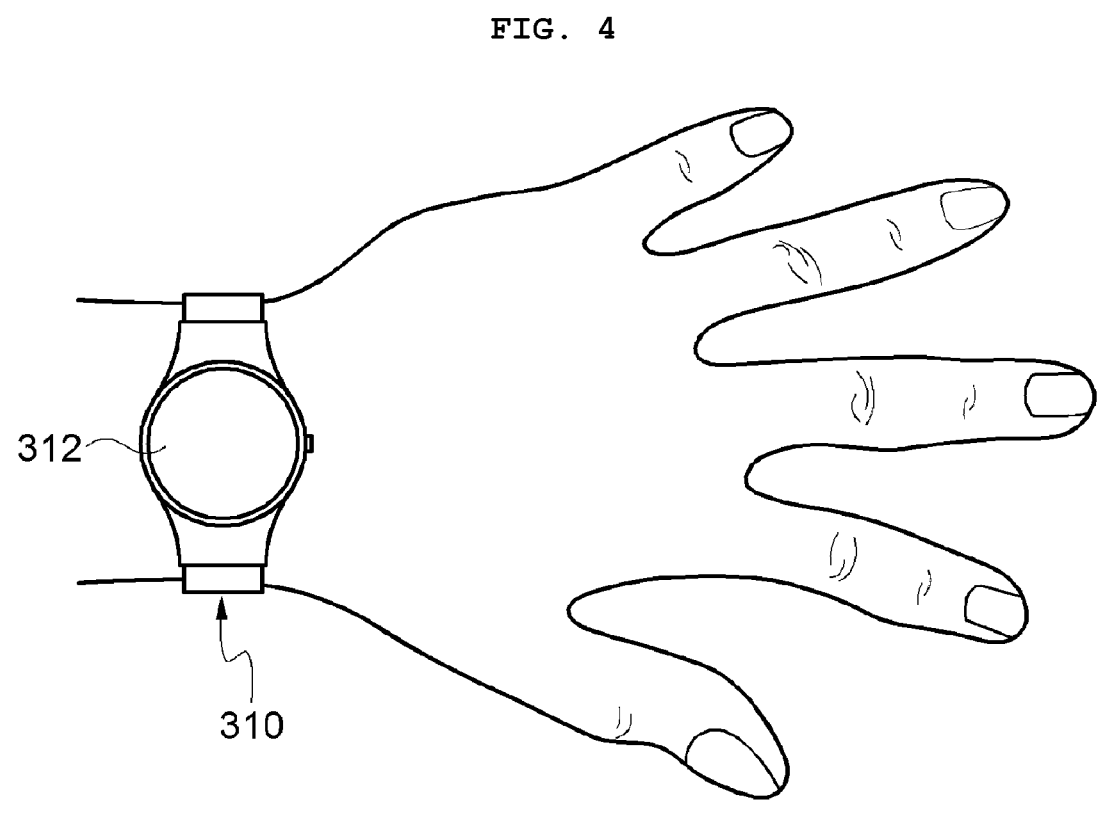
Figure 5:
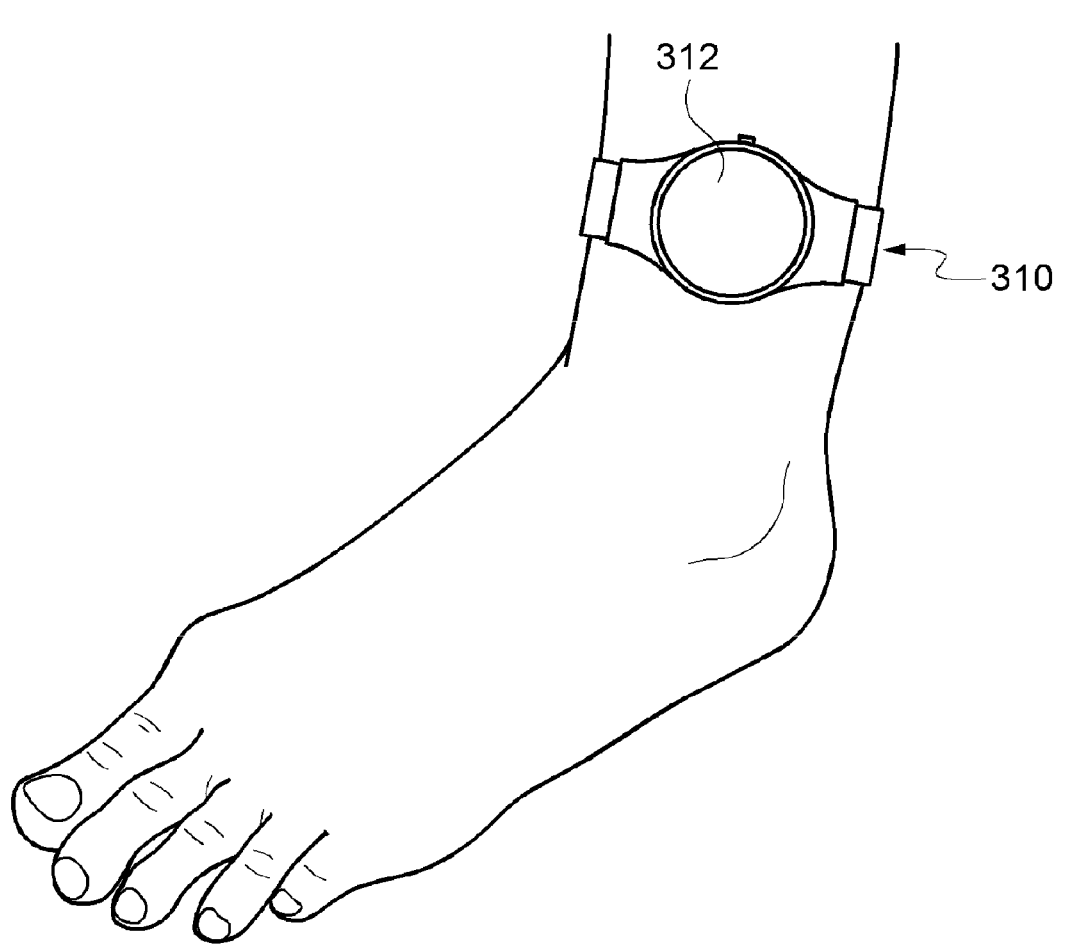
FIG. 5 is a view illustrating a state in which the band unit shown in FIG. 3 is worn on the user's ankle.
Figure 6:
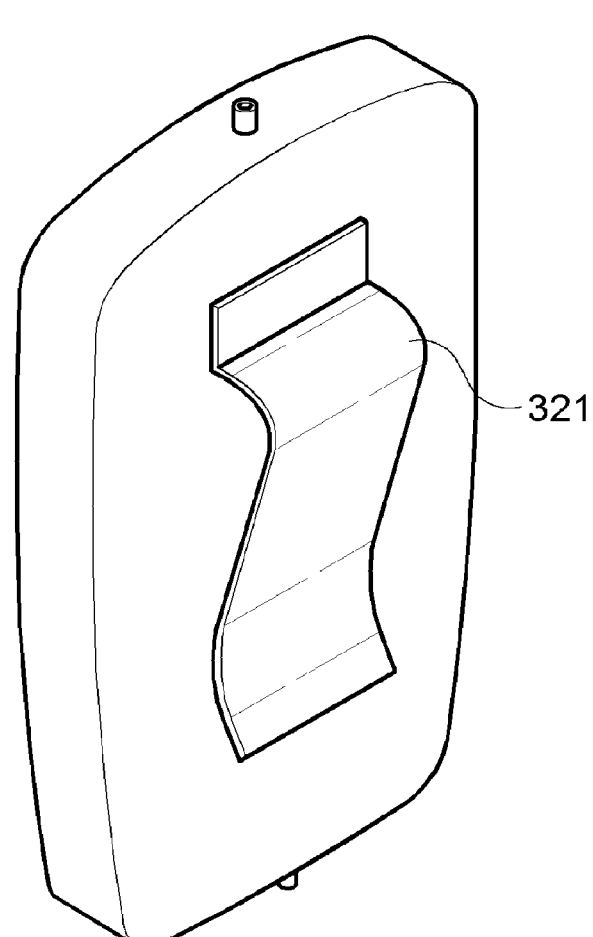
FIG. 6 is a rear view of a body unit shown in FIG. 3.

FIG. 3 is a perspective view illustrating an embodiment of the device for treating bacterial and viral diseases using electrical stimulation according to an exemplary embodiment, FIG. 4 is a view illustrating a state in which a band unit shown in FIG. 3 is worn on the user's wrist, FIG. 5 is a view illustrating a state in which the band unit shown in FIG. 3 is worn on the user's ankle, and FIG. 6 is a rear view of a body unit shown in FIG. 3.

Referring to FIGS. 3 to 6, a disease treatment device 300 may include a band unit 310 and a body unit 320.

The band unit 310 may be formed in a form of a wearable device which is worn on the user's body and comes into contact with the user's body, for example, a wristwatch type, a wrist band type, a ring type, a necklace type, an ankle band type, a thigh band type, a forearm band type or the like.

For example, the band unit 310 may be worn on the user's wrist (see FIG. 4) or on the user's ankle (see FIG. 5), but these are only exemplary embodiments, and they are not limited thereto.

The above-described electrode unit 110, the first sensor unit 210 and the second sensor unit 220 may be mounted on the band unit 310. For example, the electrode unit 110, the first sensor unit 210 and the second sensor unit 220 may be disposed to be exposed toward the user's body from one side of the band unit 310. Through this, when the user wears the band unit 310, the electrode unit 110, the first sensor unit 210 and the second sensor unit 220 may naturally come into contact with the user's body.

According to an embodiment, the band unit 310 may include an elastic material for allowing the user easy to wear it. In addition, the band unit 310 may include a length adjustment means 311 such as a button, a buckle, a Velcro fastener, or the like, which can adjust the length thereof in a state wrapped around the user's body.

According to an embodiment, the band unit 310 may include a separate cushion material capable of performing a cushioning function to reduce skin irritation in wearing. The user may wear the band unit 310 for a long period of time without discomfort through the cushion material.

According to an embodiment, the band unit 310 may include a display 312. The display 312 displays the electrical stimulation information (e.g., voltage magnitude, current magnitude, frequency, duration of each frequency, waveform) transmitted to the user, the environmental information measured by the first sensor unit 210, the biosignal measured by the second sensor unit 220 and the like.

According to an embodiment, a battery for the operation of the band unit 310 may be embedded inside of the band unit 310.

The body unit 320 may include the above-described electrical stimulation generation unit 120, the controller 130, the input unit 230, the storage unit 240, the communication unit 250 and the output unit 260 mounted thereon.

The body unit 320 may be connected to the band unit 310 through a wire L connected to a port P. The electrical stimulation generated by the electrical stimulation generation unit 120 mounted on the body unit 320 may be transmitted to the band unit 310 through the wire L, and the electrical stimulation transmitted to the band unit 310 may be applied to the user's body through the electrode unit 110 mounted on the band unit 310. Thereby, the microcurrent may be transmitted to the user's body through electrical stimulation applied to the user's body.

The port P and the wire L may be configured in an attachable/detachable manner. Since the wire L is configured to be attachable to/detachable from the port P, it has an advantage of convenient to store and use the same.

The input unit 230 may be formed on one side of the body unit 320.

The input unit 230 may include at least one button for adjusting or receiving an electrical stimulation condition such as the magnitude, frequency, duration of each frequency, and waveform, or an operating condition of the disease treatment device 300. Herein, the at least one button may include a power button capable of receiving a signal for turning on/off the body unit 320 or the disease treatment device 300. In addition, the at least one button may include another button for storing the electrical stimulation condition or the operating condition of the disease treatment device 300 or using an additional function.

According to an embodiment, as shown in FIG. 6, the body unit 320 may include a clip 321 formed on the rear surface thereof. The body unit 320 may be easily worn on clothes of the user, etc. through the clip 321.

According to an embodiment, a battery for the operation of the body unit 320 may be embedded inside of the body unit 320.

In accordance with the disease treatment devices 100, 200, and 300 according to embodiments, bacteria and viruses can be effectively killed, such that bacterial and viral diseases may be rapidly and efficiently treated.

Figure 7:
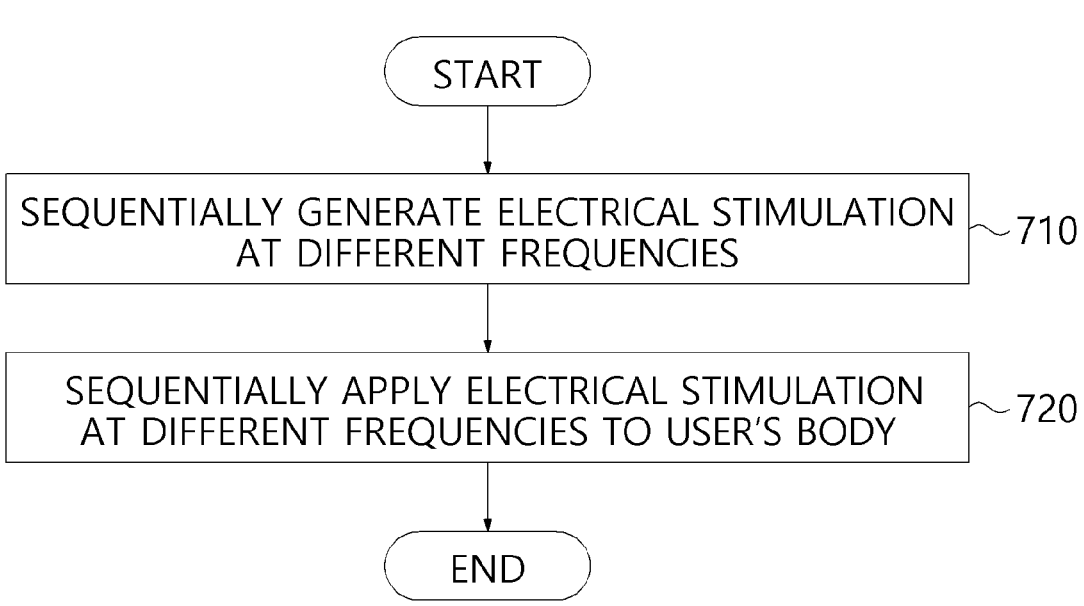
FIG. 7 is a flowchart illustrating a method for treating bacterial and viral diseases using electrical stimulation according to an exemplary embodiment.

FIG. 7 is a flowchart illustrating a method for treating bacterial and viral diseases using electrical stimulation according to an exemplary embodiment.

The method for treating bacterial and viral diseases using electrical stimulation of FIG. 7 may be performed by the disease treatment devices 100, 200 and 300 described above with reference to FIGS. 1 to 6.

Referring to FIG. 7, the disease treatment device may sequentially generate electrical stimulation at different frequencies (710). At this time, in the electrical stimulation, the voltage may be greater than 0 and 300 V or less, the current may be greater than 0 and 12 mA or less, the frequency may be 1 Hz or more and 100 GHz or less, and the duration of each frequency may be 1 minute or more and 20 minutes or less. The waveform of the electrical stimulation may be any one of direct current, alternating current, and pulsation (monophasic or biphasic pulse) or a combination of two or more thereof.

According to an embodiment, the disease treatment device may use a pre-stored frequency list, and may sequentially and repeatedly generate electrical stimulation at each frequency in the frequency list.

For example, it is assumed that three frequencies (a first frequency to a third frequency) are registered in the frequency list and the duration of electrical stimulation at each frequency is set to be 1 minute. In this case, the electrical stimulation generation unit 120 may generate electrical stimulation at the first frequency for 1 minute and transmit it to the electrode unit 110, generate electrical stimulation at the second frequency for 1 minute and transmit it to the electrode unit 110, and generate electrical stimulation at the third frequency for 1 minute and transmit it to the electrode unit 110, and then generate electrical stimulation at the first frequency again for 1 minute and transmit it to the electrode unit 110. In this way, the electrical stimulation generation unit 120 may sequentially and repeatedly generate the electrical stimulation at each frequency in the frequency list and apply it to the user through the electrode unit 110.

The disease treatment device may sequentially apply electrical stimulation at different frequencies to the user's body through the electrode unit in contact with the body of a user who has the bacterial or viral disease (720). Herein, the user's body may include a wrist, an ankle, a forearm, a calf, a thigh, a finger, a waist, a neck, and the like, but it is not limited thereto. In addition, the electrical stimulation includes a voltage or current, and may transmit a microcurrent of less than 1000 μA to the user's body through electrical stimulation.

The bacterial or viral disease may include rhinitis. In addition, the bacterial disease may include, for example, diseases resulting from pneumococcus, pyogenic bacteria, gonorrhea, brucellosis, *E. coli*, tubercular *bacillus*, typhoid *bacillus*, cholera bacteria, *Treponema pallidum, Staphylococcus aureus, Staphylococcus* and *Salmonella*, etc., and the viral disease may include, for example, diseases resulting from human papilloma virus, Ebola virus, coronavirus, SARS virus, measles virus, human immunodeficiency virus (HIV), Japanese encephalitis virus, hepatitis A, B and C viruses, herpes virus, rabies virus, influenza virus, Rhino virus, respiratory syncytial virus (RSV), flu virus, Zika virus, West Nile virus, variola virus and polio virus, etc. Herein, the human papilloma virus (HPV) may include, for example, types HPV 6, HPV 11, HPV 16, HPV 18, HPV 31, HPV 33, HPV 45, HPV 52 and HPV 58, etc., and the coronavirus may include, for example, SARS-CoV, MERS-CoV, SARS-CoV-2 and SARS-like-CoV, etc.

According to an embodiment, while the disease treatment device sequentially generates electrical stimulation at different frequencies and sequentially applies the electrical stimulation at different frequencies to the user's body, environmental information (e.g., temperature and humidity, etc.) of the user's skin in contact with the electrode unit may be measured. Further, when the measured environmental information is the set level or more, the disease treatment device may stop the generation of electrical stimulation or output a notification that the measured environmental information is the set level or more.

Experimental Example 1

*E. coli* strains were cultured overnight, and colony was suspended in phosphate buffer saline (PBS) to set $OD_{600}=0.5$, and was dispensed on two plates (first and second plates) by 2 ml.

No electrical stimulation was applied to the first plate, and electrical stimulation under the following conditions was applied to the second plate for 70 minutes.

—Conditions—

(1) Voltage is greater than 0 and 14 V or less, (2) frequencies are set as described in the frequency list of Table 1 below, (3) duration of each frequency is 1 minute, and (4) waveform is monophasic pulsation wave.

TABLE 1

| Sequence | Frequency (Hz) |
|---|---|
| 1 | 145.9 |
| 2 | 165.7 |
| 3 | 331.4 |
| 4 | 437.6 |
| 5 | 497.1 |
| 6 | 583.5 |
| 7 | 662.7 |
| 8 | 1167.0 |
| 9 | 1312.8 |
| 10 | 1325.5 |

Samples were harvested from each plate, decimally diluted in 0.45% saline, and the diluted samples were cultured overnight in tryptone soy agar (TSA) medium, then the number of colonies was counted and colony forming units (CFUs) per ml were calculated. Consequently, results shown in FIG. 8 could be obtained.

Figure 8:
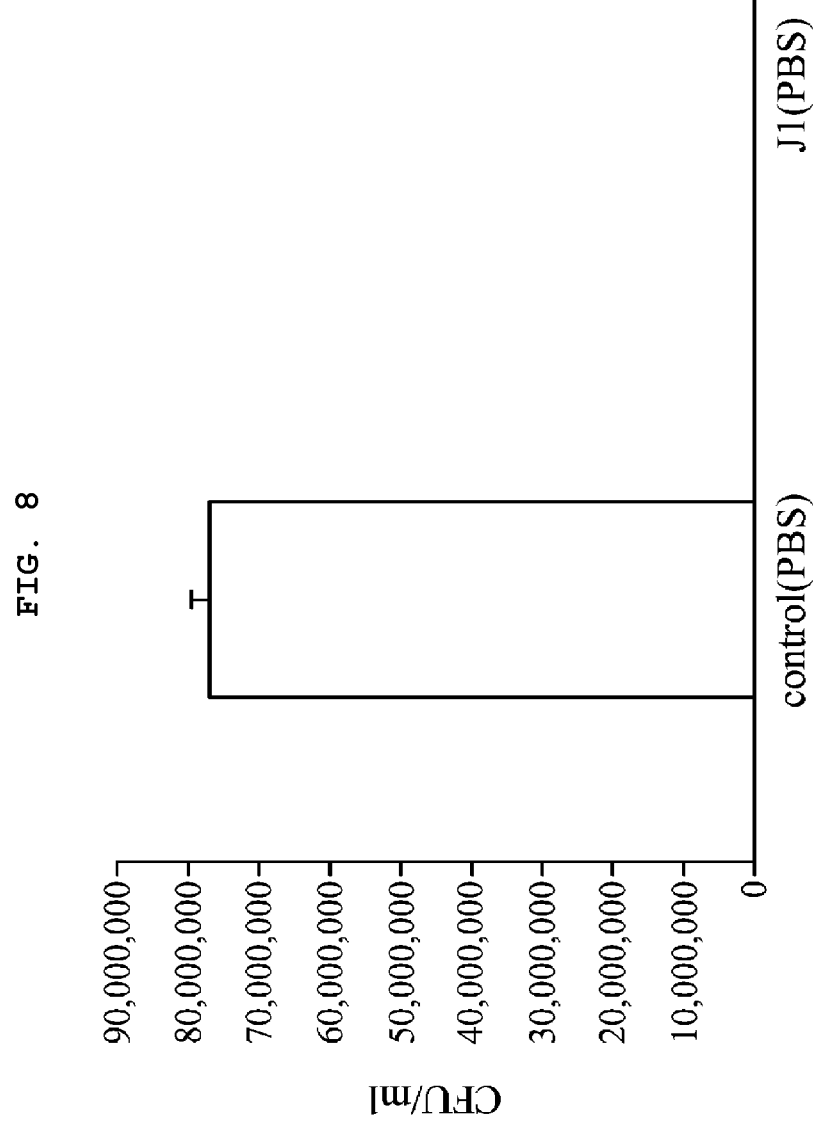
FIG. 8 is a view illustrating results of an experiment according to Experimental Example 1.

Referring to FIG. 8, it can be seen that *E. coli* bacteria were greatly reduced in the case (J1) of applying electrical stimulation compared to the case (control) of not applying electrical stimulation.

[Experimental Example 2]—Measurement of Virus Titers

As a target virus, picornavirus (enterovirus) was used, and virus titers were represented by calculating 50% Tissue Culture Infective Dose (TCID50).

Results shown in Table 2 below were obtained by applying electrical stimulation under the same conditions as in Experimental Example 1 for 60 minutes. Referring to Table 2, it can be seen that the Log 10 TCID50/ml value is significantly decreased in the case (C1) of applying electrical stimulation compared to the case (Control) of not applying the electrical stimulation.

TABLE 2

| | PEV titers (Log10 TCID50/ml) |
|---|---|
| C1 | 1.5 |
| Control | 5.5 |

[Experimental Example 3]—Verification of Rhinitis Effect

Electrical stimulation under the same conditions as in Experimental Example 1 was applied to 10 patients with allergic rhinitis for 40 minutes, and changes in the intensity of feeling rhinitis were confirmed from each patient with allergic rhinitis. Consequently, results shown in Table 3 below could be obtained. Referring to Table 3, it can be confirmed that rhinitis symptoms are alleviated when applying electrical stimulation. (In Table 3 below, the intensity of feeling rhinitis is 11 levels (0 to 10), and it means that the higher the number, the more severe the rhinitis)

TABLE 3

| | Intensity of feeling rhinitis | |
|---|---|---|
| | Before experiment | After experiment |
| Patient 1 | 8 | 2 |
| Patient 2 | 4 | 2 |
| Patient 3 | 7 | 3 |
| Patient 4 | 7 | 4 |
| Patient 5 | 9 | 3 |
| Patient 6 | 8 | 3 |
| Patient 7 | 5 | 3 |
| Patient 8 | 9 | 3 |
| Patient 9 | 4 | 3 |
| Patient 10 | 4 | 2 |

The above-described embodiments of the present invention may be implemented as a computer-readable code in a computer-readable recording medium. The computer-readable recording medium may include all types of recording devices for storing data that may be read by a computer system. Examples of computer-readable recording medium may include ROM, RAM, CD-ROM, magnetic tape, floppy disk, optical disk and the like. Further, the computer-readable recording medium may be distributed over a computer system connected by a network, and written and implemented in computer-readable code that may be read by the computer in a distributed manner.

The present invention has been described with reference to the preferred embodiments above, and it will be understood by those skilled in the art that various modifications may be made within the scope without departing from essential characteristics of the present invention. Accordingly, it should be interpreted that the scope of the present invention is not limited to the above-described embodiments, and other various embodiments within the scope equivalent to those described in the claims are included within the present invention.

What is claimed is:

1. A method for treating at least one of a bacterial disease and a viral disease, the method comprising:

sequentially generating electrical stimulation at each of different frequencies for at least three of 145.9 Hz, 165.7 Hz, 331.4 Hz, 437.6 Hz, 497.1 Hz, 583.5 Hz, 662.7 Hz, 1167.0 Hz, 1312.8 Hz, and 1325.5 Hz, with reference to a pre-stored frequency list, wherein each electrical stimulation has a waveform of a monophasic pulsation wave or an alternating current wave;

sequentially applying the generated electrical stimulation at different frequencies to a body of a user through an electrode unit in contact with the body of the user who has the at least one of the bacterial disease and the viral disease, measuring environmental information of the user's skin in contact with the electrode unit, the environmental information comprising a skin temperature and a skin humidity, and measuring biosignals of the user, the biosignals comprising a body temperature, a heart rate, and an oxygen saturation level;

transmitting the measured biosignals of the user to an external device for monitoring physical conditions of the user; and stopping generation of the electrical stimulation when the measured skin temperature and the skin humidity of the user's skin in contact with the electrode unit are equal to or higher than preset levels;

wherein the at least one of the bacterial disease and the viral disease includes at least one of a disease caused by an RNA virus of the Picornaviridae family, a disease caused by *Escherichia coli* (*E. coli*), and rhinitis, wherein the skin temperature is measured by a temperature sensor of a first sensor unit configured to measure the environmental information, the skin humidity is measured by a humidity sensor of the first sensor unit, and the body temperature is measured by a body temperature sensor of a second sensor unit configured to measure the biosignals, wherein the preset levels comprise a preset skin temperature level and a preset skin humidity level that are set to correspond to conditions in which skin temperature is increased and sweat is discharged at the user's skin in contact with the electrode unit.

2. The method according to claim 1, wherein the at least one of the bacterial disease and the viral disease comprises rhinitis.

3. The method according to claim 1, wherein the electrical stimulation comprises a voltage or current, wherein the voltage is greater than 0 and 300 V or less, the current is greater than 0 and 12 mA or less, a frequency of the electrical stimulation is 1 Hz or more and 100 GHz or less, a duration of each frequency is 1 minute or more and 20 minutes or less, and a waveform of the electrical stimulation is any one of direct current, alternating current, and pulsation or a combination of two or more thereof.

4. The method according to claim 1, wherein the at least one of the bacterial disease and the viral disease comprises the bacterial disease; and the bacterial disease further comprises diseases resulting from pneumococcus, pyogenic bacteria, gonorrhea, brucellosis, tubercular *bacillus*, typhoid *bacillus*, cholera bacteria, *Treponema pallidum, Staphylococcus aureus, Staphylococcus* and *Salmonella*.

5. The method according to claim 1, wherein the at least one of the bacterial disease and the viral disease comprises the viral disease; and the viral disease further comprises diseases resulting from human papilloma virus, Ebola virus, coronavirus, SARS virus, measles virus, human immunodeficiency virus (HIV), Japanese encephalitis virus, hepatitis A, B and C viruses, herpes virus, rabies virus, influenza virus, Rhino virus, respiratory syncytial virus (RSV), flu virus, Zika virus, West Nile virus, variola virus and polio virus.

6. An apparatus for treating at least one of a bacterial disease and a viral disease, the apparatus comprising:

an electrical stimulation generation unit configured to sequentially generate electrical stimulation at each of different frequencies for at least three of 145.9 Hz, 165.7 Hz, 331.4 Hz, 437.6 Hz, 497.1 Hz, 583.5 Hz, 662.7 Hz, 1167.0 Hz, 1312.8 Hz, and 1325.5 Hz, with reference to a pre-stored frequency list, wherein each electrical stimulation has a waveform of a monophasic pulsation wave or an alternating current wave;

an electrode unit configured to sequentially apply the generated electrical stimulation at different frequencies to user's body through an electrode unit in contact with the body of a user who has the at least one of the bacterial disease or and the viral disease, a first sensor unit configured to measure environmental information of the user's skin in contact with the electrode unit, the environmental information comprising a skin temperature and a skin humidity;

a second sensor unit configured to measure biosignals of the user, the biosignals comprising a body temperature, a heart rate, and an oxygen saturation level;

a communication unit configured to transmit the measured biosignals of the user to an external device for monitoring physical conditions of the user; and a controller configured to stop an operation of the electrical stimulation generation unit when the measured skin temperature and the skin humidity of the user's skin in contact with the electrode unit are equal to or higher than preset levels; and wherein the at least one of the bacterial disease and the viral disease includes at least one of a disease caused by an RNA virus of the Picornaviridae family, a disease caused by *Escherichia coli* (*E. coli*), and rhinitis, wherein the skin temperature is measured by a temperature sensor of the first sensor unit, the skin humidity is measured by a humidity sensor of the first sensor unit, and the body temperature is measured by a body temperature sensor of the second sensor unit, wherein the preset levels comprise a preset skin temperature level and a preset skin humidity level that are set to correspond to conditions in which skin temperature is increased and sweat is discharged at the user's skin in contact with the electrode unit.

7. The apparatus according to claim 6, wherein the at least one of the bacterial disease and the viral disease comprises rhinitis.

8. The apparatus according to claim 6, wherein the electrical stimulation comprises a voltage or current, wherein the voltage is greater than 0 and 300 V or less, the current is greater than 0 and 12 mA or less, a frequency of the electrical stimulation is 1 Hz or more and 100 GHz or less, a duration of each frequency is 1 minute or more and 20 minutes or less, and a waveform of the electrical stimulation is any one of direct current, alternating current, and pulsation or a combination of two or more thereof.

9. The apparatus according to claim 6, further comprising:

a band unit on which the electrode unit is mounted and configured to be worn on the user's body to come into contact with the user's body; and a body unit on which the electrical stimulation generation unit is mounted and configured to be connected to the band unit through a wire.

10. The apparatus according to claim 9, wherein the band unit is formed in a form of a wrist band type or an ankle band type, and is worn on the user's wrist or on the user's ankle.

11. The apparatus according to claim 6, wherein the bacterial disease further comprises a disease resulting from at least one of pneumococcus, pyogenic bacteria, gonorrhea, brucellosis, tubercular *bacillus*, typhoid *bacillus*, cholera bacteria, *Treponema pallidum, Staphylococcus aureus, Staphylococcus* and *Salmonella*.

12. The apparatus according to claim 6, wherein the viral disease further comprises a disease resulting from at least one of human papilloma virus, Ebola virus, coronavirus, SARS virus, measles virus, human immunodeficiency virus (HIV), Japanese encephalitis virus, hepatitis A, B and C viruses, herpes virus, rabies virus, influenza virus, Rhino virus, respiratory syncytial virus (RSV), flu virus, Zika virus, West Nile virus, variola virus and polio virus.

\* \* \* \* \*